(12) United States Patent
Muratori et al.

(10) Patent No.: US 11,452,439 B2
(45) Date of Patent: Sep. 27, 2022

(54) DEVICE FOR ACCOMMODATING SURGICAL TOOL PRIOR TO AND DURING MEDICAL PROCEDURES

(71) Applicant: Covidien LP, Mansfield, MA (US)

(72) Inventors: Adam Muratori, Providence, RI (US); Bill Kane, Providence, RI (US); David Fink, Providence, RI (US); Joe Gordon, Providence, RI (US); Mark Guarraia, Providence, RI (US); Paul Bertram, Providence, RI (US); Paul Puniello, Providence, RI (US); Justin Morse, Providence, RI (US)

(73) Assignee: COVIDIEN LP, Mansfield, MA (US)

( * ) Notice: Subject to any disclaimer, the term of this patent is extended or adjusted under 35 U.S.C. 154(b) by 397 days.

(21) Appl. No.: 15/544,047

(22) PCT Filed: Jan. 21, 2016

(86) PCT No.: PCT/US2016/013349
§ 371 (c)(1),
(2) Date: Jul. 17, 2017

(87) PCT Pub. No.: WO2016/115310
PCT Pub. Date: Jul. 21, 2016

(65) Prior Publication Data
US 2018/0263481 A1    Sep. 20, 2018

Related U.S. Application Data

(60) Provisional application No. 62/103,871, filed on Jan. 15, 2015.

(51) Int. Cl.
*A61B 1/12*    (2006.01)
*A61B 1/00*    (2006.01)
(Continued)

(52) U.S. Cl.
CPC .......... *A61B 1/127* (2013.01); *A61B 1/00057* (2013.01); *A61B 1/3132* (2013.01); *A61B 90/70* (2016.02); *A61B 2090/701* (2016.02)

(58) Field of Classification Search
CPC ............ A61B 1/00057; A61B 1/00131; A61B 1/00137; A61B 1/12; A61B 1/121;
(Continued)

(56) References Cited

U.S. PATENT DOCUMENTS 5,549,543 A    8/1996  Kim
6,068,815 A *  5/2000  Oberleitner ............ A01N 59/00
                                                        134/22.12
(Continued)

FOREIGN PATENT DOCUMENTS

CN    101374452 A    2/2009
CN    101564284 A    10/2009
(Continued)

OTHER PUBLICATIONS

Supplementary European Search Report for Serial No. EP 16 73 7858 dated Jul. 17, 2018.
(Continued)

*Primary Examiner* — Ryan N Henderson
(74) *Attorney, Agent, or Firm* — McCormick, Paulding & Huber PLLC

(57) ABSTRACT

A device may be configured for white balancing a medical videoscopic camera system prior to videoscopic medical procedures, as well as optionally simultaneously or non-simultaneously applying a fog-prohibiting agent to the distal lens of a medical videoscope such as an endoscope or laparoscope. The device combines a white balancing mechanism, protective mechanism, and defogging mechanism in one simple easy to use device.

20 Claims, 6 Drawing Sheets

(51) Int. Cl.
*A61B 90/70* (2016.01)
*A61B 1/313* (2006.01)

(58) Field of Classification Search
CPC ......... A61B 1/122; A61B 1/123; A61B 1/125; A61B 1/126; A61B 1/127; A61B 1/128; A61B 90/70; A61B 2090/701; A61B 2090/702; H04N 9/73; H04N 9/735
See application file for complete search history.

(56) References Cited

U.S. PATENT DOCUMENTS

| | | | |
|---|---|---|---|
| 6,377,848 B1 | 4/2002 | Garde et al. | |
| 6,793,882 B1* | 9/2004 | Verschuur | A61L 2/26 206/439 |
| 6,929,136 B2 | 8/2005 | Salazar-Leal | B65D 51/245 374/162 |
| 7,311,660 B2 | 12/2007 | Gomez | |
| 7,537,129 B2* | 5/2009 | Bayss | B65D 51/249 374/161 |
| 8,152,717 B2 | 4/2012 | Gomez | |
| 8,470,601 B2* | 6/2013 | Foley | A61L 2/26 422/26 |
| 2002/0022762 A1 | 2/2002 | Beane et al. | |
| 2002/0193752 A1* | 12/2002 | Lynn | A61B 10/0045 604/249 |
| 2003/0080130 A1* | 5/2003 | Goetz | B65D 17/401 222/548 |
| 2003/0127415 A1* | 7/2003 | Carballido | B65D 41/42 215/230 |
| 2004/0076777 A1* | 4/2004 | Bayss | B65D 51/249 428/34.1 |
| 2006/0047239 A1* | 3/2006 | Nita | A61B 17/22004 604/22 |
| 2006/0293564 A1* | 12/2006 | Nishiie | A61B 1/121 600/156 |
| 2007/0293818 A1* | 12/2007 | Stout | G09F 3/0291 604/93.01 |
| 2008/0021381 A1* | 1/2008 | Lurvey | G01N 21/78 604/87 |
| 2008/0021392 A1 | 1/2008 | Lurvey et al. | |
| 2008/0161646 A1 | 7/2008 | Gomez | |
| 2009/0112057 A1 | 4/2009 | Kammer et al. | |
| 2011/0092775 A1* | 4/2011 | Deshmukh | A61B 17/0218 600/204 |
| 2012/0067349 A1* | 3/2012 | Barlow | A61M 16/0644 128/205.25 |
| 2012/0082589 A1* | 4/2012 | Ladison | A47K 3/127 422/26 |
| 2013/0019374 A1* | 1/2013 | Schwartz | A61F 13/041 428/492 |
| 2013/0058844 A1* | 3/2013 | Shick | B65D 41/0471 422/558 |
| 2013/0333796 A1* | 12/2013 | Py | A61J 1/1425 141/1 |
| 2014/0001142 A1* | 1/2014 | Wu | A61J 9/02 215/11.2 |

FOREIGN PATENT DOCUMENTS

| | | |
|---|---|---|
| EP | 2111808 A2 | 10/2009 |
| JP | 2001095928 A | 4/2001 |
| JP | 2001255631 A | 9/2001 |
| JP | 2009525068 A | 7/2009 |
| JP | 2013165805 A | 8/2013 |

OTHER PUBLICATIONS

Chinese Office Action and English Translation for Serial No. 201680005954.9 dated May 5, 2019.
Chinese Office Action and English Translation for Serial No. 201680005954.9 dated Aug. 29, 2018.
International Search Report for (PCT/US2016/013349) date of completion is Jul. 21, 2016 (4 pages).
Japanese Office Action and English Translation for Serial No. 2017537269 dated Sep. 17, 2019.

* cited by examiner

DEVICE FOR ACCOMMODATING SURGICAL TOOL PRIOR TO AND DURING MEDICAL PROCEDURES

CROSS-REFERENCE TO RELATED APPLICATIONS

This application is a U.S. National Stage Application filed under 35 U.S.C. § 371(a) of International Patent Application No. PCT/US2016/013349, filed Jan. 14, 2016, which claims the benefit of and priority to U.S. Provisional Patent Application No. 62/103,871, filed Jan. 15, 2015, the entire disclosure of which is incorporated by reference herein.

TECHNICAL FIELD

This invention generally relates to a device for cleaning and/or calibrating certain surgical tools used during a surgical procedure.

BACKGROUND

Endoscopic video devices have been used during surgery to provide a better view of a surgical site. These video devices have been known to require periodic calibration and cleaning as they get fogged up and/or covered with bodily fluids. Some portable endoscopic cleaning and calibration devices have included a cleaning liquid or gel that is heated with a battery powered heating element. The endoscope was then inserted into a chamber in the cleaning device containing the heated cleaning liquid to clean the endoscope.

While these cleaning devices were easy to use, the devices had limited storage options due to presence of the cleaning liquid and batteries as well as the need to maintain sterility and operability of the device while in storage. Additionally, while the devices were designed to be single-use disposable devices, they did not include features clearly alerting the surgical staff as to sterility status of device.

There is a need for powered surgical cleaning devices containing cleaning liquids or gels that are able to maintain the sterility and/or operability of the device for longer periods in storage and/or transport. There is also a need for these devices to clearly alert surgical staff as to the sterility status of device and prevent patient harm from the inadvertent reuse of a non-sterile previously used cleaning device.

SUMMARY

A device for accommodating a surgical tool may include a housing having an outer surface defining an opening. An interior of the housing may define a canal for receiving a surgical tool. The canal may have a first end coupled to the opening and a second end terminating within the housing. The device also may include a sealing tab for insulating battery contact prior to the use of the device. Once the sealing tab is removed, the battery makes contact with the battery contact to activate the device.

The sealing tab may further include a liquid sealing portion for providing sealing for defogging material.

The device may include a pull out portion formed within the housing to allow access to the interior of the device so that the batteries may be removed after the initial use of the device.

The device may include an extra seal disposed about the opening to provide extra sealing and to provide an indication when the device may be ready for use.

The device may include an opening adapter to effectively reduce the diameter of the opening for accommodating smaller diameter surgical tools and to close the opening during shipping.

BRIEF DESCRIPTION OF THE DRAWINGS

These objects and features of the invention will be more clearly understood from the following detailed description along with the accompanying drawing figures, wherein.

DETAILED DESCRIPTION

Figure 1:
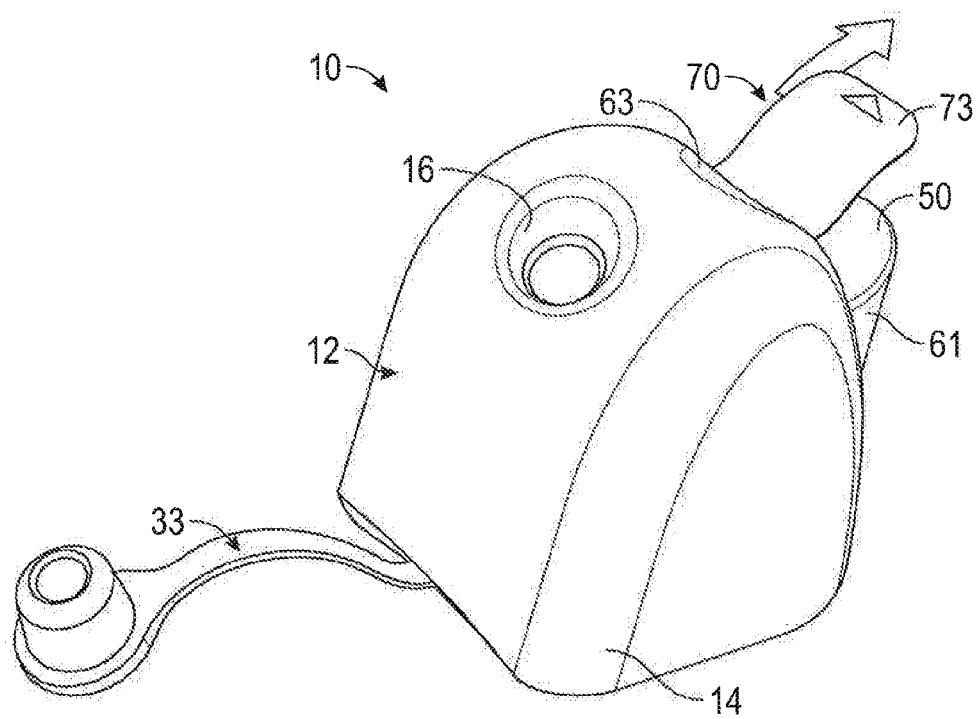
FIG. 1 is a perspective view of an embodiment of a device including a sealing tab.
Figure 2:
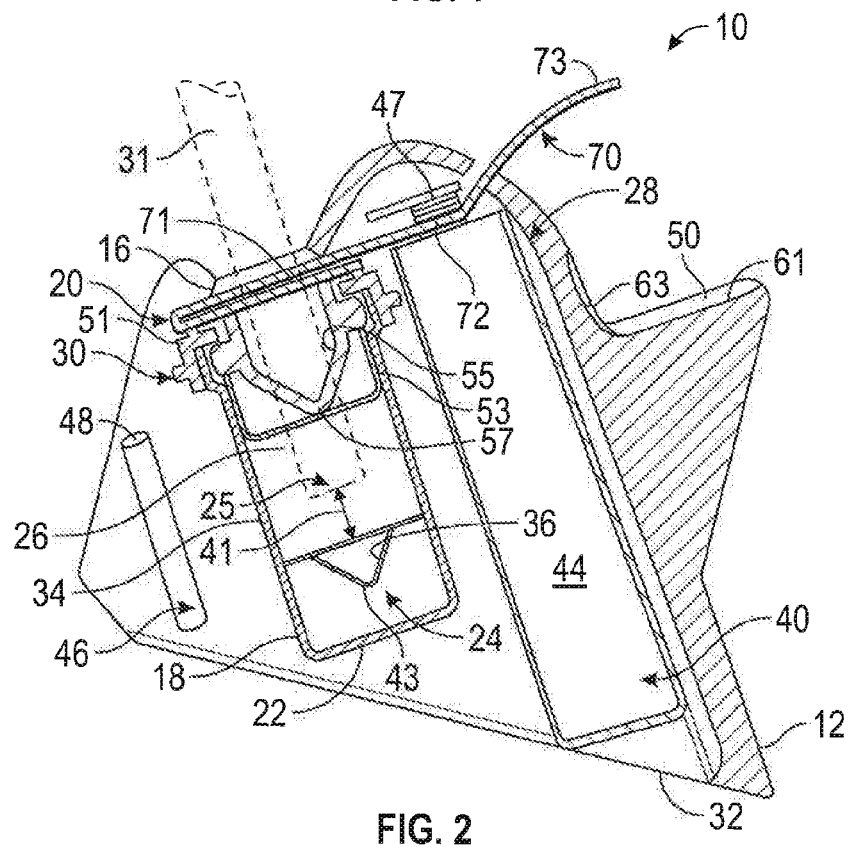
FIG. 2 is a cross-sectional diagram of the device of FIG. 1.

With reference to FIGS. 1 and 2, a device 10 may include a housing or outer shell 12. The housing 12 may have an outer surface 14 defining an opening 16 for inserting therein a medical videoscope such as a laparoscope or endoscope or any other surgical tool 31. An interior of the housing 12 defines a canal 18 having a first end 20 coupled to the opening 16 and a second end 22 terminating within the housing 12 for receiving a distal lens of a medical videoscope. A white balancing reference material 24 may be disposed within the housing 12 adjacent to the second end 22 of the canal 18.

A defogging material 26 may be stored in the canal 18 adjacent to the second end 22 and used to treat and/or prevent the distal lens 25 of a medical videoscope 31 from fogging during a medical procedure. The device 10 may include a heating mechanism 28 thermally coupled to the canal 18 for heating an interior wall of the canal and the surgical defogging material 26 disposed within the canal to further prevent the distal lens of a medical videoscope from fogging. Heating mechanism 28 may also be thermally coupled to the canal 18 to heat an interior wall of the canal to prevent a distal lens of a medical videoscope disposed in the canal from fogging when no defogging material may be disposed in the canal. The device 10 may include a self-sealing mechanism 30 disposed at least partly within the canal 18. The mechanism 30 may allow a medical videoscope to penetrate the seal and make contact with the surgical defogging material 26 while preventing the surgical defogging material from spilling out of the canal.

The housing or shell 12 may be made of an insulating foam material such as a medical grade polyurethane foam or another shock absorbing insulating material. The shell 12 may be designed to protect the lens of a medical videoscope or any other type of instrument from damage prior, during, and after a surgical procedure. An outer cover of the shell 12 may be constructed of high density polyurethane, etha, viscoelastic, latex foams, and the like. The outer cover may also be made of another material such as rubber-like foam, semi-flexible thermoplastic, insulating cardboard, thick insulating fabric, or a plastic frame covered by a silicone or insulating plastic. The outer cover may be selected to have good shock absorbing and insulating properties.

The device 10 may be shaped as in FIG. 1 or in any other practical shape such as a cube, square, spherical, or tubular shape. The device 10 may have rounded corners or square corners. The exterior dimensions may vary. In some instances, the device 10 may be about 4 inches long, 3.5 inches wide, and 4 inches high. In other instances, it may be between as about 15 mm to 6 inches wide, 1 to 6 inches long, and 15 mm to 8 inches high. In other instances the dimensions may vary further and/or the device 10 may be sized to accommodate the shape of any medical instrument used.

The device 10 may include a securing mechanism 32, as seen in FIG. 2, coupled to a bottom of the housing 12. For example, the securing mechanism 32 may be a solid flap, which may have approximately same perimeter as the base of the housing 12. This flap may be attached only either at the front or rear or side bottom part of the device 10 so as to create a hinge. The flap may be attached in the middle by two elastic bands. The flap may be constructed of a high-density foam material, cardboard, plastic, or a microfiber material. The external face of the bottom flap may have an adhesive material that may have a protective cover until it may be needed.

When surgery begins and the surgeon brings the device 10 up to the operative field, the surgeon may secure the device anywhere on top of the drapes by removing a protective cover from an adhesive bottom of the securing mechanism 32 and securing the device 10 anywhere on the operative field. The device 10 may also be secured by an assistant to a sterile equipment tray, from which a medical videoscope may then be passed to the surgeon. The securing mechanism 32 may be a flap so that the scope may be inserted vertically. When not in use, the flap 32 allows the device 10 to rotate horizontally and rest on the drapes while the scope remains inside the device. Although the device 10 may rotate along the hinge of the flap 32, the flap may still maintain the device 10 securely attached to the drape with the adhesive coating.

Alternatively, the device 10 may be constructed without the flap 32 and adhesive may be placed directly on the bottom of the device. Furthermore, the device 10 may be secured to any surface through such components such as, but not limited to, adhesives, screws, magnetism, mounts, and clips. Moreover, the device 10 may remain unsecured to any surface and be put on and pulled off the scope as needed during the medical procedure.

Figure 3:
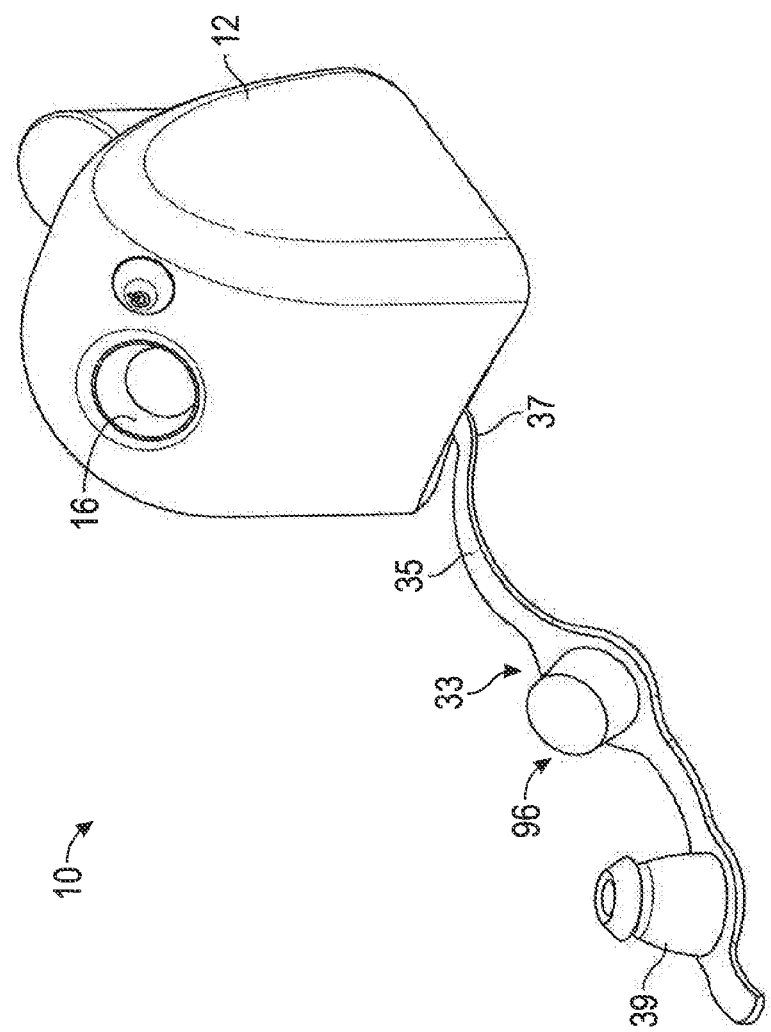
FIG. 3 is a perspective view of a further embodiment of a device having an opening adapter with a plug portion.
Figure 4:
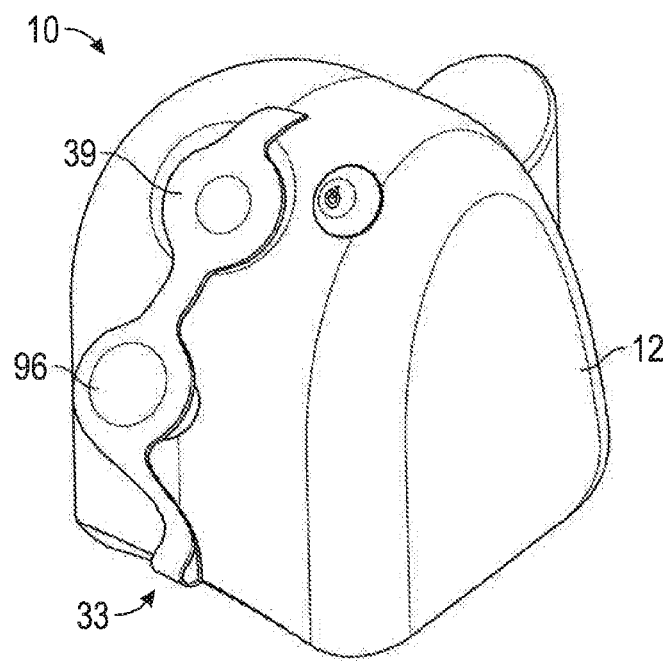
FIG. 4 is a perspective view of the device of FIG. 3 shown in use.
Figure 5:
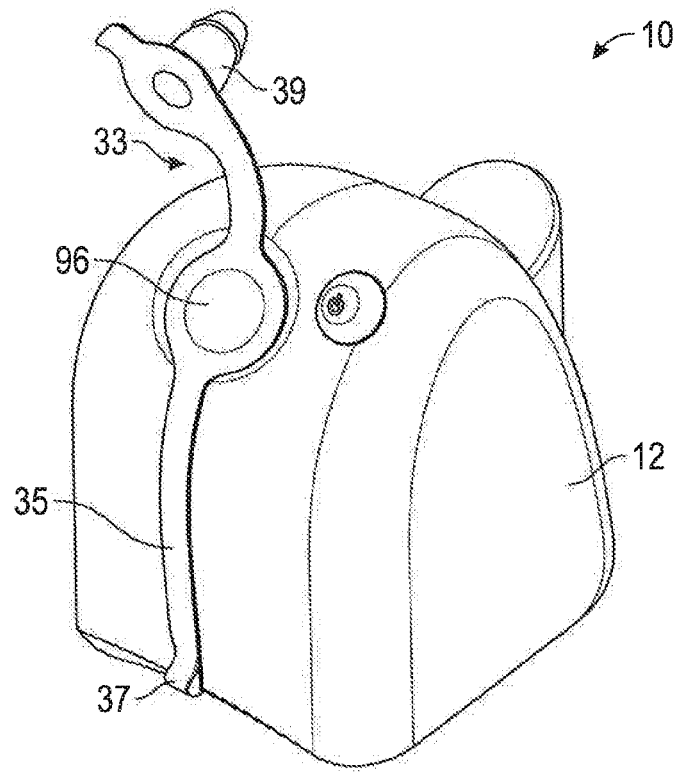
FIG. 5 is a perspective view of the device of FIG. 3 shown during shipping.

As shown in FIGS. 3-5, the device 10 may include an opening adapter 33 to effectively reduce the diameter of the opening 16 for accommodating smaller diameter surgical tools and to close the opening 16 during shipping. The adapter 33 may include a flexible longitudinal stem 35 having a base portion 37 at one end of the stem and a reduced opening portion 39 at another end of the stem. As shown in FIGS. 3-5, the base portion 37 may be coupled to a lower portion of the housing 12. The flexible longitudinal stem 35 may be bendable in order to insert the reduced opening portion 39 into the opening 16 of the housing 12, as shown in FIG. 4. The opening adapter 33 may be made of a flexible medical grade silicone plastic, but may also be constructed out of other flexible materials. The diameter of the reduced opening portion 39 is shown by way of example to be 5 mm, but need not be 5 mm and may vary in other instances. The adapter 33 also may include a plug portion 96 for use during shipping to ensure that the defogging material does leak out of the device 10. Thus, as shown in FIGS. 4 and 5, the plug portion 96 may close the opening 16 during shipment and the reduced portion 39 may close the opening 16 during the use of the device 10.

Referring back to FIG. 2, the device 10 may include an inner chamber or center sheath 34 defining the canal 18 and accommodated within a cavity of the housing 12. The canal 18 and the center sheath 34 are sized and shaped to accommodate a medical videoscope or surgical tool 31 when inserted therein. The canal 18 and the sheath 34 extend directly down the center of the device 10 from an upper front to a lower back portion. The sheath 34 may alternatively extend directly down a center or lateral to a center of the device 10. The location of the sheath 34 may be in any configuration as long as uniform thermal conductivity may be achieved. The length of the sheath 34 may be about 3 inches long, but may also be other lengths including, but not limited to, between 0.5 to 8 inches. The sheath 34 may have the shape of a tube. The tubular diameter inside the sheath may be about 5 mm, 10 mm, or any other diameter depending on the size and shape of the medical instrument to be inserted therein. The sheath 34 may be constructed of stainless steel, aluminum, high-density polyurethane foam, etha foam, viscoelastic foam, latex foam, rubber-like foam, thin plastic, water impermeable fabric, silicon, a rubber-like material, or any materials. The sheath 34 may all be white or any other color.

As mentioned above, the self-sealing mechanism 30 may be disposed at least partly within the canal 18 and the sheath 34 to prevent the surgical defogging material 26 from spilling out of the opening 16 of the device 10. The canal 18 or the sheath 34 may accommodate the defogging material 26 such as an antifog, lens cleaning agent, or surfactant solution, and may lead into or define a reservoir which may be filled with the defogging material.

The self-sealing mechanism 30 may have the shape of a tube within a tube, shown in FIG. 2. The self-sealing mechanism 30 may be made of a flexible medical grade silicone plastic. The self-sealing mechanism 30 may be configured to allow a medical videoscope to enter a reservoir at the second end 22 of the canal 18 or inner end of the sheath 34, make contact with the defogging material 26, and/or prevent a liquid or gel defogging material from spilling out of the opening 16 of the housing 12 when the device 10 is turned upside down and the scope is removed from the device. In other words, the self-sealing mechanism 30 may be configured to function as a type of one-way valve to prevent fluid or gel from leaking.

In one embodiment, the self-sealing mechanism 30 may include an upper lip 51 seated on the first end 20 of the sheath 34. The self-sealing mechanism 30 further may include three flaps or pockets 53 oriented downwardly from the upper lip 51 and spaced from one another circumferentially about a periphery of the self-sealing mechanism 30 such that the pockets are facing an inner surface of the sheath 34. The self-sealing mechanism 30 may have a center tube or duck bill 55 oriented downwardly from the upper lip 51 that defines a slit 57 at a bottom portion thereof for permitting the scope 31 to pass therethrough. The center tube 55 may be spaced radially inwardly of the pockets 53 so as to define a space between the center tube and the pockets.

The self-sealing mechanism 30 may prevent liquid from spilling out by creating and trapping liquid in the space around a first end 20 of the canal 18 or the sheath 34 defining the canal. When the sheath 34 may be turned with the reservoir downward, all the liquid falls into the reservoir. As the sheath 34 and the reservoir are turned upside down, the liquid slides along the side of the sheath 34 and enters the space of the self-sealing mechanism 30 surrounding a distal end of the sheath 34. The pockets 53 relieve pressure caused by a scope entering the reservoir. With a sealed enclosure provided by the center tube 55, as the scope 31 may be inserted through the center tube 55, pressure builds as the scope takes up space within the reservoir. The center tube or duck bill 55 may be configured to prevent fluid or air from escaping, and thus the pressure build-up tries to force the scope out of the reservoir. The pockets 53 may overcome such detrimental pressure build-up upon the scope. As the pressure builds, instead of pushing the scope out of the reservoir, the pockets may deform taking up less space and balancing out the pressure. In other words, the pockets 53 are configured to serve as a pressure compensating system of the self-sealing mechanism 30.

Alternatively, the self-sealing mechanism may resemble a heart valve or be made with a flap and a hinge that only opens in one direction. The self-sealing mechanism may also resemble a valve in a human vein. Moreover, the self-sealing mechanism may be a ball and socket mechanism in which a ball inside the reservoir plugs the hole when the reservoir may be turned upside down but still allows for the scope to enter in the other direction. The self-sealing mechanism may be constructed from a resilient plastic or other rubber-like material. It may also be made from a high-density foam or water impermeable fabric. The self-sealing mechanism may also be made of metal, aluminum, or silicone plastic. The self-sealing mechanism may be any configuration known to a person skilled in the art to prevent leakage and splash back of fluid.

As shown in FIG. 2, the white balancing reference material 24 may be disposed adjacent to the second end 22 of the canal 18 such that when a lens of a scope may be placed into the reservoir, the lens approaches within a predetermined distance of the reference material 24. The white balancing reference material 24 may be a true white, soft, non-scratch, absorbent material. The material must have a good light diffusing property. The white balancing reference material 24 may include a sponge having a white color with a chromaticity of about D-65 or about a D-50 or about D-100. The white color of the white balancing reference material 24 may be equal parts of red, blue and green, but may have slight deviations designed to match the camera system specifications of a medical videoscope 31 to be white balanced by the reference material. The white balancing reference material 24 may be any desired shape including but not limited to a square, rectangle, ellipse, or circle. The shape of the reference material 24 may be dependent on the shape of the scope to be white balanced. The reference material 24 may be about ¼ to about 1/16 of an inch thick in some instances but may vary in other instances. The reference material 24 may be made out of a low density foam or other soft material which may be either hydrophobic or hydrophylic. The reference material 24 may be made out of white medical grade closed cell foam.

Referring to FIG. 2, the reference material 24 may define an indentation or narrowing portion 36 which may be small enough for the distal lens 25 of a surgical tool, such as a videoscope, 31 to come into contact with the narrowing portion 36 and not further enter the reference material. The narrowing portion 36 may maintain a predetermined space or distance 41 between the lens and a white surface of a facing base portion 43 of the reference material. The space 41 may be of a sufficient distance to allow for proper white balancing of the videoscope 31.

The defogging material 26, in the form of a gel or liquid, may be made of, but need not be limited to, a combination of water, glycol, and a water-soluble wetting agent, alcohol, and a gelling agent. When in the form of a liquid, the defogging material 26 may also be made from 1 part poloxamer 188, 99 parts water. A commercially available wound cleaning surfactant solution such as Shurclenz™ may also be diluted with water and used. Other non-ionic surfactants may be used alone or in a mixture. Alcohol may also be used in some instances. If a gelling agent is used, it may be a starch or any super absorbent polymer. Alternatively, any commercially available surgical defogging solution (e.g. F.R.E.D.™ or E.L.V.I.S.™) may be used.

With reference to FIG. 2, the heating mechanism 28 may be disposed adjacent to the reservoir of the second end 22 of the canal 18 or the sheath 34 so as to be in thermal communication therewith. The sheath 34 and the reservoir as part of the sheath may be made of stainless steel or aluminum for efficient heat transfer from the heating mechanism 28 to the defogging material 26 disposed within the reservoir. The heating mechanism 28 may include, for example, a heating element (not shown) such as a wound gauge copper wire or nichrome wire. The wire may be connected to a power source 40 such as a battery pack having a housing made of plastic or to another source such as an AC outlet. When activated, electricity flows from the power source 40 through the heating element so as to heat the reservoir and the defogging material 26 disposed therein.

A thermistor or switch (not shown) having a thermal component may be placed in the electrical circuit of the heating mechanism 28 to turn off the flow of electricity when a predetermined temperature may be reached by the defogging material 26 so as to allow the heating mechanism to maintain a constant temperature of the defogging material above body temperature for an extended period of time while being energized by the power source 40. Power source 40 may include any type of power source including but not limited to batteries 44 electrically connected in series. Although the device, for example may have four AAA batteries 44, different size and different quantities of batteries may be used. A trigger or plunger (not shown) may be coupled to the switch. The plunger may be made of stainless steel, aluminum, plastic, or other generally rigid material. When the plunger is pressed downwardly into the housing, the plunger initially closes the switch to electrically energize the heating mechanism 28 until the thermal component of the switch opens the electrical circuit when the defogging material reaches the predetermined temperature.

Referring to FIGS. 1 and 2, in one embodiment, the device 10 for accommodating the surgical tool 31 therein may include a sealing tab 70 to seal the canal 18 or sheath 34 and to insulate battery contacts during storage and shipping. The tab 70 may include a liquid sealing tab portion 71, a battery sealing tab portion 72, and an exposed tab portion 73 such that the liquid sealing portion 71 and the battery sealing portion 72 are disposed within the device 10 and the exposed tab portion 73 may extend outside of the device 10. The liquid sealing portion 71 of the tab 70 may be disposed between an opening 16 of the device 10 and a self-sealing mechanism 30 and may provide sealing for the canal 18 or sheath 34 so that defogging material 26 does not spill out during storage and shipping of the device 10. The battery sealing tab portion 72 of the tab 70 may be disposed between the batteries 44 and battery contacts 47. The battery sealing tab portion 72 may provide a protective barrier between the batteries 44 and battery contacts 47 before the device 10 is used. When the tab 70 is removed from the device 10 by being pulled out by the exposed tab portion 72, the liquid sealing portion 71 may be removed from the canal 18 and the battery sealing portion 72 may be removed from protecting the batteries 44 such that the device 10 may be activated once the batteries 44 and the battery contacts 47 are connected. Although the sealing tab 70 may be shown to have both the liquid sealing portion 71 and a battery sealing portion 72, the sealing tab may include only one of the two portions.

The device 10 may include an alert mechanism 46 to notify a user that at least a portion of the device is being heated by the heating mechanism 28. For example, the alert mechanism 46 may include a light such as an LED 48 or an audible tone generator. Alternatively, a thermometer or heat sensitive paint may be used as an indicator of activation of the heating mechanism 28.

Figure 7:
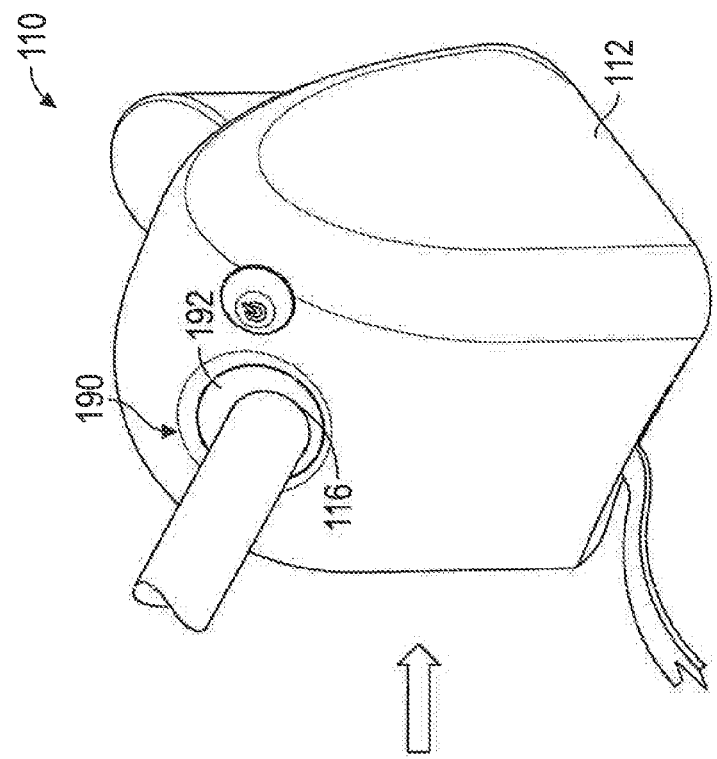
FIG. 7 is a perspective view of the device of FIG. 6.
Figure 6:
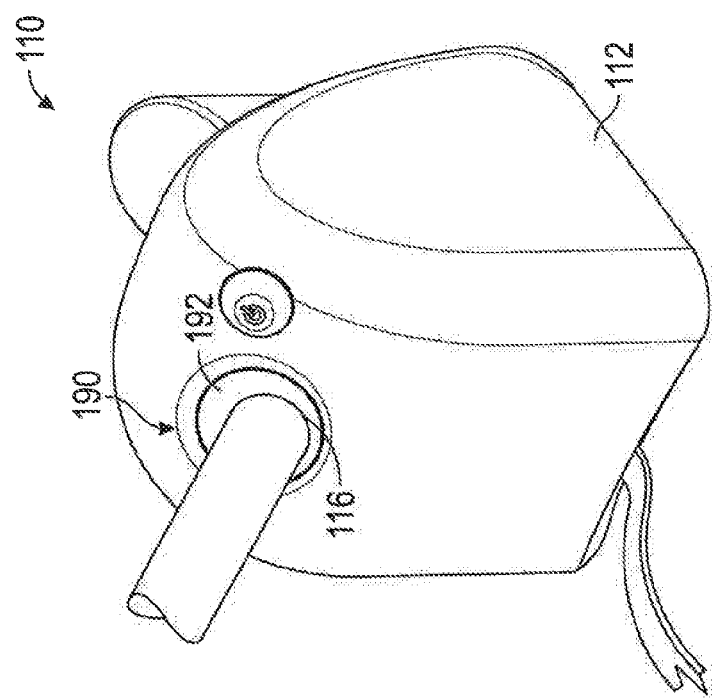
FIG. 6 is a perspective view of a further embodiment of a device having an extra seal.
Figure 8:
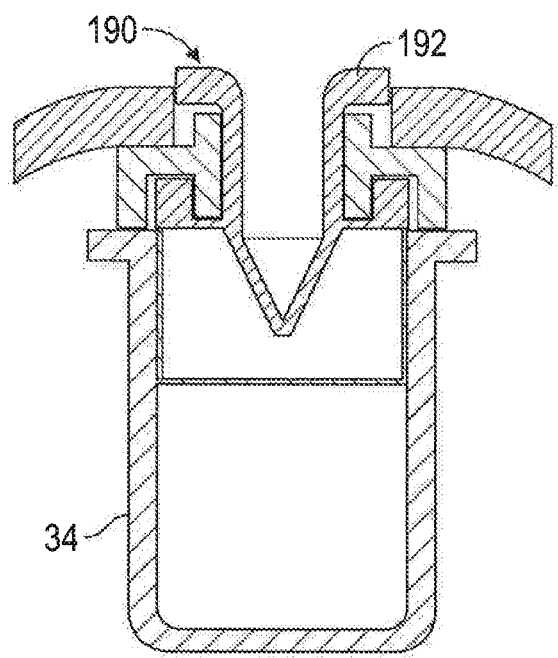
FIG. 8 is a cross-sectional diagram of the device of FIG. 6.

Referring to FIGS. 6, 7 and 8, in an alternative embodiment, a device 110 may include an extra seal 190 with a warm up indicator 192. The extra seal 190 may be disposed about the opening 116 of the device 110 and may be visible from the outside of the device. The seal 190 may change color when the device heats up to indicate that the device may be ready for use. The extra seal 190 may be fabricated from thermo-chromic elastomeric material or the like and may include colorant therein to indicate color change when the device heats up to show to the user that the device may be ready for use. Thus, the seal 190 may serve a dual purpose of providing additional sealing and of providing an indication that the device may be ready for use.

The device 10 may also have a microfiber fabric 50 on all or part of the outer surface 14 of the housing 12 so that a scope lens may be wiped thereon and cleaned during a surgical procedure. The housing 12 may define a ledge 61 and a depressed surface portion 63 which may be covered by the microfiber 50 and against which a scope may be wiped clean. The microfiber 50 may be either permanently or removably attachable to the device 10. The microfiber 50 may be, but may be not limited to, any combination of polyester and nylon.

As mentioned above, the sheath 34 and the reservoir may be constructed of stainless steel or aluminum, but any metal with good heat transfer properties may be used.

Because a medical videoscope may be submerged in the defogging material, the device 10 may reduce the risk of a fire hazard as hot light from the scope may be not allowed to concentrate on a drape or on the patient when the scope is submerged in the defogging material.

The device 10 may also be packaged in combination with other medical videoscopic care products such as microfiber surgical sponges, trocar wipes, and a microfiber patient cleaning set. A kit containing this white balancing and defogging device in combination with other medical videoscopic care products may be called a "laparoscopic care kit" or a "laparoscopic care pack."

The device 10 may be oriented to maintain a videoscope such as, for example, laparoscope 31 or any other surgical tool, inserted therein in an upright position. Alternatively, the device 10 may be oriented to maintain the laparoscope 31 inserted therein in a resting position. The securing mechanism 32 of the device 10 may serve as a hinge. The adhesive in the bottom of the device 10 may allow the device to be secured to drapes or to a table and still allow for the scope 31 to rest freely. This may enable the scope 31 to remain inside the device 10 so as to prevent a fire hazard whenever the scope is not in use.

Figure 9:
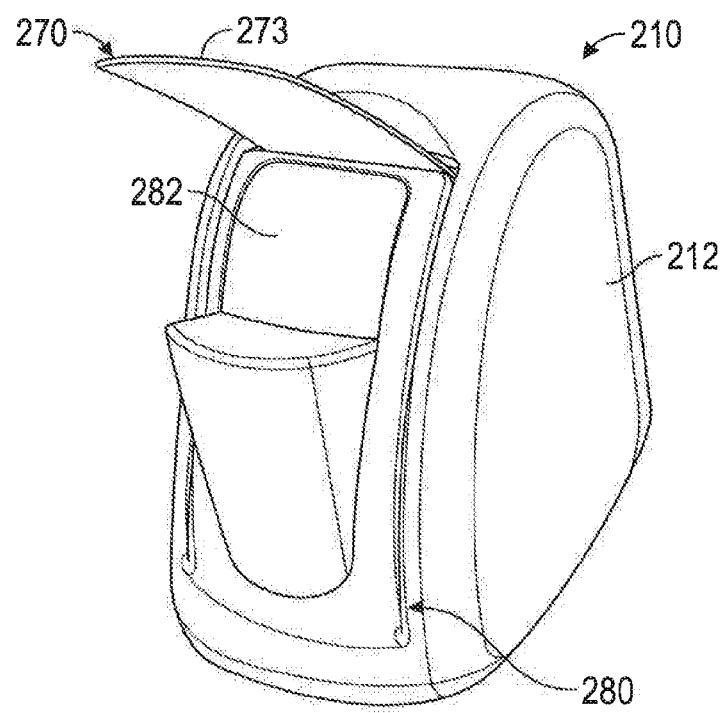
FIG. 9 is a perspective view of another embodiment of a device including a pull out portion with a detail line.
Figure 10:
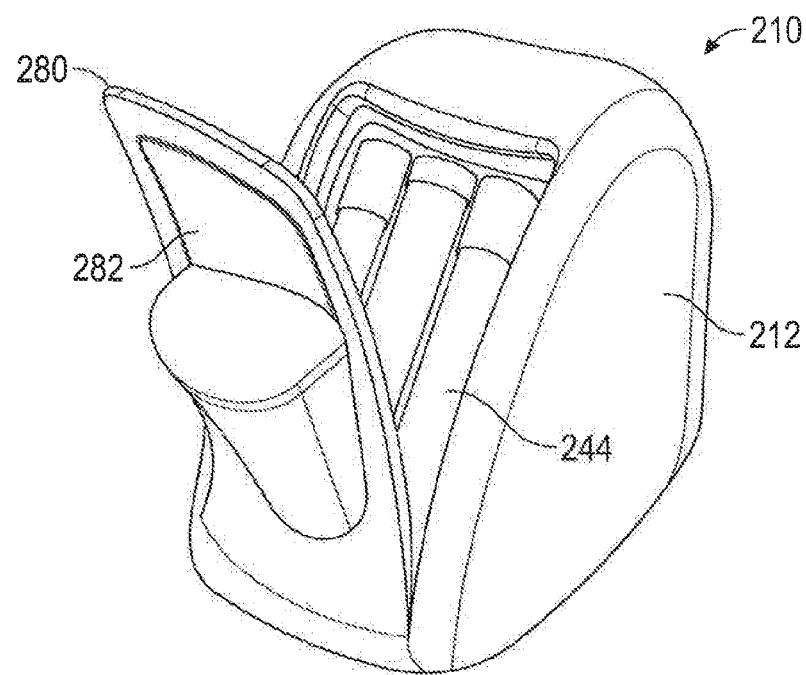
FIG. 10 is a perspective view of the device of FIG. 9 with the pull out portion in an open position.

Referring to FIGS. 9 and 10, in another embodiment, a device 210 may include a detail line 280 formed within housing 212 of the device 210 to define a pull out portion 282 therein. The detail line 280 is shown as having a U-shaped contour, but other shapes may be formed. The detail line 280 may be formed to allow easy tear path for removal of batteries 244 and destruction of the device 210. The pull out portion may be easily moved into an open position, as shown in FIG. 10, to expose the batteries 244. Once the batteries 244 are exposed, the batteries may be removed. Thus, after the device 210 has been used, the pull out portion 282 may be pulled along the detail line 280 from the device 210 to separate from the housing 212 into an open position and to expose batteries 244 for removal to prevent unsafe reuse of the device 210.

Figure 11:
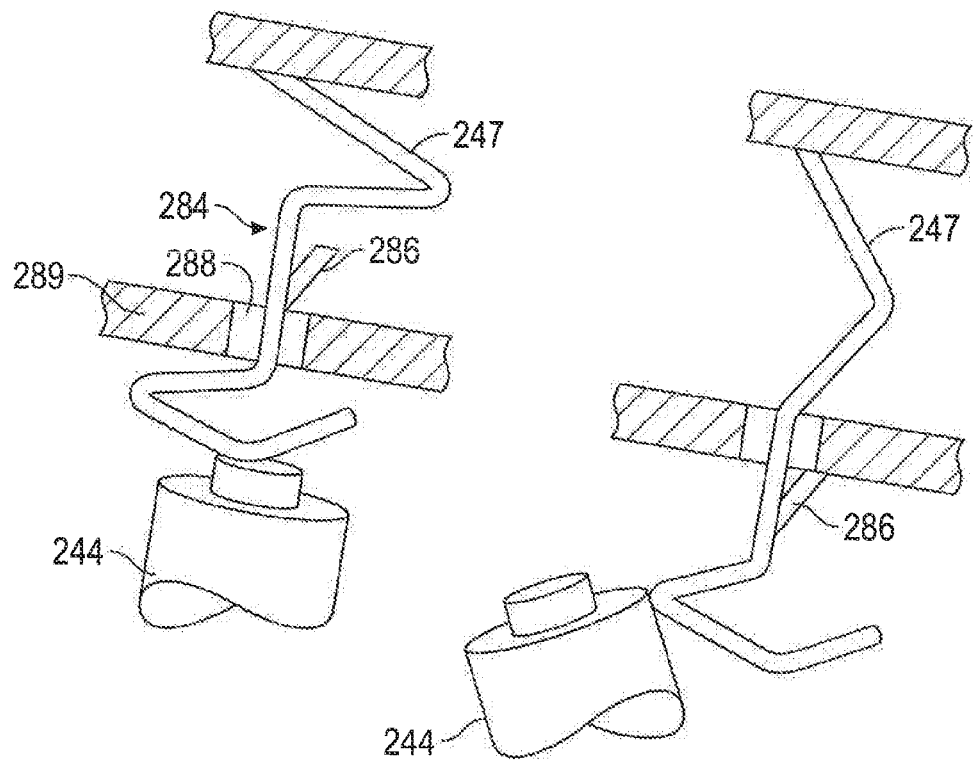
FIG. 11 is a cross-sectional diagram of a latch mechanism disposed with another embodiment of the device of FIG. 9.

Referring to FIG. 11, in a further embodiment, a latch mechanism 284 may be included to ensure that the device may be not reused after the initial intended use. The latch mechanism 284 may include a detent 286 disposed on a battery contact 247. As the batteries 244 are dislodged from the original position, the spring-loaded contact 247 may expand through an opening 288 formed in a wall 289 such that the detent passes through the opening 288 and engages the wall 289. Once the batteries 244 have been moved from the original position, the latch mechanism 284 may activate to preclude re-insertion of the batteries and reuse of the device.

While the above invention may have been described with reference to certain preferred embodiments, the scope of the present invention may be not limited to these embodiments. For example, although the white balancing reference material and defogging material are shown and described as being part of a single device, it should be understood that the white balancing reference material and defogging material may be disposed in separate devices working either simultaneously or non-simultaneously with one another without departing from the scope of the present invention. One skilled in the art may find other variations of these preferred embodiments which, nevertheless, fall within the scope and spirit of the present invention.

What is claimed is:

1. A device for accommodating a surgical tool comprising:
    a housing having an outer surface defining an opening, an interior of the housing defining a canal for receiving a surgical tool, the canal having a first end coupled to the opening and a second end terminating within the housing such that the second end is closed within the housing; and
    a seal disposed about the opening to provide sealing and configured to provide an indication when the device is warmed up by a heating element of the device and ready for use;
    wherein the seal is configured to provide sealing on the surgical tool while the surgical tool is inserted through the seal.

2. The device according to claim 1 wherein the seal is fabricated from a material that changes color upon heating.

3. The device according to claim 2 wherein the material of the seal is a thermo-chromic elastomeric material.

4. The device according to claim 1 wherein the indication is visible when the surgical tool is received within the canal.

5. The device according to claim 1, further comprising:
at least one battery for powering the device, the battery coming into contact with a battery contact; and
a sealing tab having a battery sealing portion configured to insulate the battery contact prior to the use of the device.

6. The device according to claim 1, further comprising:
a pull out portion formed within the housing and configured to allow access to the interior of the device.

7. The device according to claim 1, further comprising:
an opening adapter configured to close the opening during shipping.

8. A device for accommodating a surgical tool comprising:
a housing having an outer surface defining an opening, an interior of the housing defining a canal for receiving a surgical tool, the canal having a first end coupled to the opening and a second end terminating within the housing; and
a seal disposed about the opening to provide sealing and configured to provide an indication when the device is warmed up by a heating element of the device and ready for use,
wherein the indication is visible when the surgical tool is received within the canal; and
wherein the seal is configured to provide sealing on the surgical tool while the surgical tool is inserted through the seal.

9. The device according to claim 8 wherein the seal is fabricated from a material that changes color upon heating.

10. The device according to claim 8 wherein the seal is fabricated from a thermo-chromic elastomeric material.

11. The device according to claim 8, further comprising:
at least one battery for powering the device, the battery coming into contact with a battery contact; and
a sealing tab having a battery sealing portion configured to insulate the battery contact prior to the use of the device.

12. The device according to claim 8, further comprising:
a pull out portion formed within the housing and configured to allow access to the interior of the device.

13. The device according to claim 8, further comprising:
an opening adapter configured to close the opening during shipping.

14. A device configured to defog an endoscope, the device comprising:
a housing having an outer surface defining an opening, an interior of the housing defining a canal for receiving the endoscope, the canal having a first end coupled to the opening and a second end terminating within the housing such that the second end is closed within the housing;
a heating element disposed within the housing:
a battery disposed within the housing configured to power the heating element;
a seal disposed about the opening to seal about the endoscope and configured to change color upon heating providing a visual indication the device is ready to use.

15. The device according to claim 14, wherein the seal is fabricated from a material that changes color upon heating.

16. The device according to claim 14, wherein the seal is fabricated from a thermo-chromic elastomeric material.

17. The device according to claim 14, further comprising:
the battery coming into contact with a battery contact; and
a sealing tab having a battery sealing portion configured to insulate the battery contact prior to the use of the device.

18. The device according to claim 14, further comprising:
a pull out portion formed within the housing and configured to allow access to the interior of the device.

19. The device according to claim 14, further comprising:
an opening adapter configured to close the opening during shipping.

20. The device according to claim 14, wherein the seal is configured to provide sealing while the surgical tool is inserted through the seal.

* * * * *